United States Patent
Xiao et al.

(10) Patent No.: US 10,254,434 B2
(45) Date of Patent: *Apr. 9, 2019

(54) NUCLEAR MAGNETIC RESONANCE LOGGING INSTRUMENT PROBE WITH MULTI-LAYERED MAGNET AND ANTENNA EXCITATION METHOD

(71) Applicant: CHINA UNIVERSITY OF PETROLEUM-BEIJING, Beijing (CN)

(72) Inventors: Lizhi Xiao, Beijing (CN); Guangzhi Liao, Beijing (CN); Qunjie Du, Beijing (CN); Sihui Luo, Beijing (CN)

(73) Assignee: CHINA UNIVERSITY OF PETROLEUM-BEIJING, Beijing (CN)

( * ) Notice: Subject to any disclaimer, the term of this patent is extended or adjusted under 35 U.S.C. 154(b) by 295 days.

This patent is subject to a terminal disclaimer.

(21) Appl. No.: 15/258,767

(22) Filed: Sep. 7, 2016

(65) Prior Publication Data
US 2017/0082773 A1    Mar. 23, 2017

(30) Foreign Application Priority Data

Sep. 23, 2015 (CN) .......................... 2015 1 0614309

(51) Int. Cl.
*G01V 3/32*    (2006.01)
*G01R 33/34*    (2006.01)
(Continued)

(52) U.S. Cl.
CPC .............. *G01V 3/32* (2013.01); *G01N 24/081* (2013.01); *G01R 33/3415* (2013.01); *G01R 33/383* (2013.01); *G01R 33/3808* (2013.01)

(58) Field of Classification Search
CPC .. G01V 3/32; G01R 33/3808; G01R 33/3415; G01R 33/383; G01R 33/445; G01N 24/081
(Continued)

(56) References Cited

U.S. PATENT DOCUMENTS 6,255,817 B1 * 7/2001 Poitzsch .............. G01N 24/081
324/300
2003/0210050 A1  11/2003 Prammer et al. ............ 324/315
(Continued)

FOREIGN PATENT DOCUMENTS

CN    101098047 A    1/2008
CN    102519999 A    6/2012
(Continued)

OTHER PUBLICATIONS

The Chinese First Examination Report of corresponding Chinese patent application No. 201510614309.4, dated Jun. 23, 2017.

*Primary Examiner* — Rishi R Patel
(74) *Attorney, Agent, or Firm* — J.C. Patents

(57) ABSTRACT

The present invention provides a nuclear magnetic resonance logging instrument probe with multi-layered magnet and an antenna excitation method, the nuclear magnetic resonance logging instrument probe includes a probe skeleton, multiple magnet assemblies and a plurality of antennas; the probe skeleton is of a cylindrical shape, multiple magnet assemblies are distributed in the circumferential direction of the probe skeleton; the magnet assembly includes at least two layers of magnet arranged from top to bottom, the magnet is magnetized in a radial direction, two adjacent layers of magnet are magnetized in opposite directions; an antenna is arranged outside each magnet assembly, multiple antennas are independently fed. In the nuclear magnetic resonance logging instrument probe and antenna excitation method, through exciting different antennas, (Continued)

detection of stratum information at different azimuth angles is realized, which improves circumferential resolution of the probe, realize stratum detection in three dimensions along radius, axis and circumference.

14 Claims, 4 Drawing Sheets

(51) Int. Cl.
*E21B 49/00* (2006.01)
*G01V 3/14* (2006.01)
*G01N 24/08* (2006.01)
*G01R 33/3415* (2006.01)
*G01R 33/38* (2006.01)
*G01R 33/383* (2006.01)

(58) Field of Classification Search
USPC .......................................... 324/303, 318–322
See application file for complete search history.

(56) References Cited

U.S. PATENT DOCUMENTS

| 2008/0174309 | A1  | 7/2008 | Pusiol et al. | 324/306 |
| 2017/0082772 | A1* | 3/2017 | Xiao | G01V 3/32 |
| 2017/0082775 | A1* | 3/2017 | Xiao | G01V 3/32 |

FOREIGN PATENT DOCUMENTS

| CN | 203594440 U | 5/2014 |
| CN | 203867568 U | 10/2014 |

* cited by examiner

NUCLEAR MAGNETIC RESONANCE LOGGING INSTRUMENT PROBE WITH MULTI-LAYERED MAGNET AND ANTENNA EXCITATION METHOD

CROSS-REFERENCE TO RELATED APPLICATION

This application claims priority to Chinese Patent Application No. 201510614309.4, filed on Sep. 23, 2015, which is hereby incorporated by reference in its entirety.

TECHNICAL FIELD

The invention relates to the field of nuclear magnetic resonance logging technology and, in particular, to a nuclear magnetic resonance logging instrument probe and an antenna excitation method.

BACKGROUND

Immediately following its discovery in 1946, nuclear magnetic resonance (Nuclear Magnetic Resonance, NMR) phenomenon found application in the fields such as physics, chemistry, material science, life science and medicine. And the application of nuclear magnetic resonance in petroleum and natural gas industry, pioneered by utilization in the field of reservoir petrophysics, was initiated in the 1950s. A nuclear magnetic resonance logging instrument can perform stratum information detection around a wellbore by using the principle of nuclear magnetic resonance, and is thus provided with a unique capacity for qualitative identification and quantitative evaluation of reservoir fluid.

Probe is one of the important parts of a nuclear magnetic resonance logging instrument, and its structure determines key performances such as measurement mode, nuclear magnetic resonance region and nuclear magnetic resonance signal intensity of the instrument. A nuclear magnetic resonance logging instrument probe mainly includes a magnet and an antenna, where the magnet can form a static magnetic field for polarizing a self-spinning hydrogen proton, while the antenna can transmit a radio frequency field for turning the self-spinning hydrogen proton around. Removing of the radio frequency field prompts the self-spinning hydrogen proton to precess along the static magnetic field, resulting in that nuclear magnetic resonance induction signals, detection of which makes it possible to analyze the stratum condition.

In the prior art, a nuclear magnetic resonance logging instrument probe usually adopts a cylindrical magnet, in which two sides of a circular face of the magnet serve as an N pole and an S pole, respectively, and closed magnetic induction lines directed from the N pole to the S pole form magnetic field distribution; an antenna encircles the magnet, allowing excitation of a polarized stratum region around the wellbore in 360 degrees, thus making the region around the wellbore free of detection blind area, and enabling multi-frequency multi-section measurement, but since the measured signal can only be an average signal of the signals in a stratum of 360 degrees, the nuclear magnetic resonance logging instrument probe in the prior art can only conduct signal detection in a radial depth dimension and an axial depth dimension, and is incapable of carrying out signal detection of multi-directional sensitive region in the circumferential direction.

SUMMARY

The present invention provides a nuclear magnetic resonance logging instrument probe and an antenna excitation method, for addressing the technical problem in the prior art that the nuclear magnetic resonance logging instrument probe can only conduct signal detection in a radial depth dimension and an axial depth dimension, and is incapable of carrying out signal detection of multidirectional sensitive region in the circumferential direction.

The present invention provides a nuclear magnetic resonance logging instrument probe, including: a probe skeleton, a plurality of magnet assemblies and a plurality of antennas;

the probe skeleton is of a cylindrical shape, and the plurality of the magnet assemblies are evenly distributed in the circumferential direction of the probe skeleton;

the magnet assembly includes at least two layers of magnets arranged sequentially from top to bottom, the magnet is magnetized in a radial direction, and the two adjacent layers of magnet of the magnet assembly are magnetized in opposite directions;

an antenna is arranged on the outside of each of the magnet assemblies, and each of the plurality of antennas is independently fed.

Further, the antenna is formed by winding an oxide-skin-free copper sheet, and is of a nested-multi-hollow-square type or a nested-multi-hollow-circle type.

Further, the antenna includes N turns of oxide-skin-free copper sheets, the distance between a $1^{th}$ and a $2^{th}$ turn equals to that between a $N-1^{th}$ and a $N^{th}$ turn, and the distance between a $k^{th}$ turn and a $k+1^{th}$ turn is greater than that between the $1^{th}$ and the $2^{th}$ turn;

where, both k and N are natural numbers, and $2<k<N-1$, $N>3$.

Further, an auxiliary antenna is arranged on the outside of each of the antennas and is fed independently from the antenna.

Further, each of the magnet assemblies includes three layers of magnet, i.e. an upper layer, a middle layer and a lower layer, where, thickness of the middle layer magnet is smaller than that of the upper layer magnet and the lower layer magnet.

Further, a plurality of holding cavities are arranged in the probe skeleton to match with the magnet, and the plurality of magnets are respectively arranged in the plurality of holding cavities in a fixed manner.

Further, a plurality of grooves are processed on the probe skeleton for the plurality of antennas to be respectively arranged therein in a fixed manner.

Further, the nuclear magnetic resonance logging instrument probe also includes an antenna excitation device for feeding the antenna; and the antenna excitation device includes a plurality of excitation channels, and the plurality of antennas are electrically connected with a plurality of the excitation channels, respectively.

Further, a through hole is arranged in the probe skeleton, and a central axis of the through hole coincides with a central axis of the probe skeleton;

a support bracket is provided which passes through the through hole and is fixedly connected with a probe housing, or, a fluid guide pipe for drilling fluid to run through is provided which passes through the through hole and is fixedly connected with the probe skeleton via a metal piece.

The present invention also provides an antenna excitation method based on the nuclear magnetic resonance logging instrument probe described by any one of the aforementioned technical solutions, including:

exciting one antenna, in order to realize detection of downhole single azimuth angle;

exciting at least two antennas, in order to realize detection of downhole multiple azimuth angles; and exciting all the antennas, in order to realize detection of downhole omnidirectional detection.

In the nuclear magnetic resonance logging instrument probe and the antenna excitation method provided by the present invention, a plurality of magnet assemblies are evenly distributed in the circumferential direction of the probe skeleton, and an antenna is arranged on the outside of each magnet assembly, and each of the plurality of antennas is independently fed. Through exciting different antennas, detection of stratum information at different azimuth angles may be realized, thereby improving circumferential resolution of the nuclear magnetic resonance logging instrument probe, and realizing stratum detection in three dimensions in the directions of radius, axis and circumference. Furthermore, each magnet assembly includes at least two layers of magnet which are sequentially arranged from top to bottom, and two adjacent layers of magnet are magnetized in opposite directions, so as to gather magnetic induction lines more close together, and distribute magnetic field strength of a static magnetic field more evenly at the same radial depth and different axial depths, thus improving performance of the nuclear magnetic resonance logging instrument probe.

Figure 1:
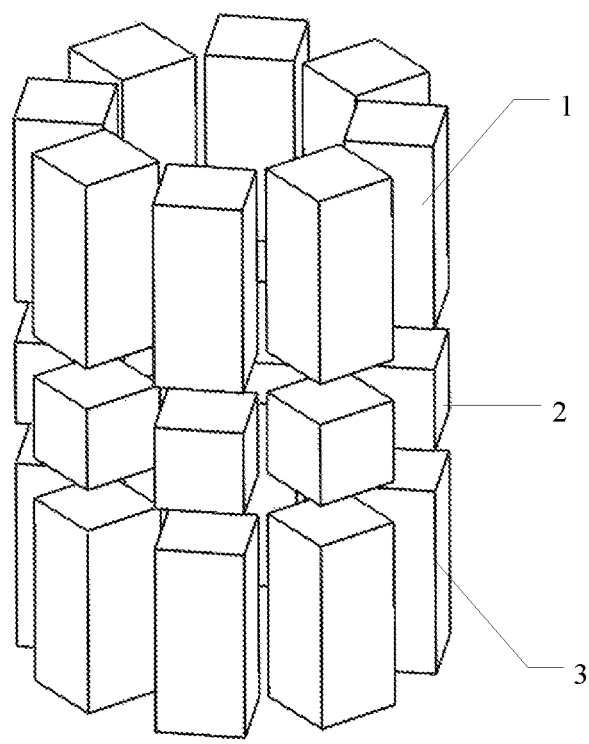
FIG. 1 is a structural diagram for a plurality of magnet assemblies of a nuclear magnetic resonance logging instrument probe provided by an embodiment of the present invention.

Reference Numerals in the Accompanying FIGS:
1—upper layer magnet; 2—middle layer magnet; 3—lower layer magnet; 4—antenna of nested-multi-hollow-square type; 5—antenna of nested-multi-hollow-circle type

DESCRIPTION OF EMBODIMENTS

In order to make objective, technical solutions and advantages of embodiments of the present invention clearer, the technical solutions in the embodiments of the present invention will be clearly and completely described in conjunction with accompanying figures in the embodiments of the present invention hereafter, and apparently, the described embodiments are just part rather than all of the embodiments of the present invention. All the other embodiments obtained by one of ordinary skill in the art based on the embodiments in the present invention without creative effort shall belong to the protection scope of the present invention.

Embodiment 1

A nuclear magnetic resonance logging instrument probe is provided in the embodiment of the present invention. In this embodiment, the nuclear magnetic resonance logging instrument probe may include: a probe skeleton, a plurality of magnet assemblies and a plurality of antennas; where the probe skeleton is of a cylindrical shape, and the plurality of magnet assemblies are evenly distributed in the circumferential direction of the probe skeleton.

FIG. 1 is a structural diagram for a plurality of magnet assemblies of a nuclear magnetic resonance logging instrument probe provided by Embodiment 1 of the present invention. As shown in FIG. 1, the probe includes eight magnet assemblies, each magnet assembly includes at least two layers of magnet sequentially arranged from top to bottom, where the magnet is magnetized in a radial direction, and two adjacent layers of magnet of the magnet assembly are magnetized in opposite directions; and an antenna is arranged on the outside of each magnet assembly, and each of the plurality of antennas is independently fed.

Specifically, the plurality of magnet assemblies may form a centro-symmetric structure, the distance between each magnet assembly and the central axis of the probe skeleton is equal, and the plurality of magnet assemblies are evenly distributed in the circumferential direction of the probe skeleton.

Each magnet assembly includes at least two layers of magnet sequentially arranged from top to bottom, and the magnet is magnetized in the radial direction, meaning that the magnet is magnetized in an extending direction of the radius of the probe skeleton. Specifically, the magnet may be magnetized in a direction from the inside out or from the outside inward. Additionally, two adjacent layers of magnet of each magnet assembly are magnetized in opposite directions, in which the middle layer magnet 2 may be magnetized in a direction from the inside out, and correspondingly, the upper layer magnet 1 and the lower layer magnet 3 are magnetized in a direction from the outside inward.

In this embodiment, each magnet assembly includes a plurality of layers of magnet, and each layer of magnet is magnetized in an opposite direction, enabling to gather magnetic induction lines more close together, and to distribute the magnetic field strength of a static magnetic field at the same radial depth and different axial depths more evenly, thereby improving performance of the nuclear magnetic resonance logging instrument probe.

Preferably, the thickness of the middle layer magnet 2 is smaller than that of the upper layer magnet 1 and the lower layer magnet 3, enabling to distribute the magnetic field strength outside the magnet assembly more evenly.

An antenna is arranged outside each magnet assembly, and a plurality of antennas are independently fed, therefore, sending an excitation signal to one of the antennas will not affect the other antennas.

In practical operation, after a probe goes downhole, hydrogen protons at a plurality of azimuth angles in the circumferential direction are excited by a static magnetic field generated by a plurality of magnet assemblies, and when it is required to detect information of stratum at a certain azimuth angle, an excitation signal may be sent to an antenna corresponding to the azimuth angle, and a radio frequency magnetic field generated by the antenna can turn the hydrogen proton around; and after sending of the excitation signal to the antenna is stopped, the hydrogen proton will precess along the static magnetic field, resulting in that a nuclear magnetic resonance induction signal, detection of which may allow to obtain information of stratum the corresponding single azimuth angle. Likewise, exciting of at least two antennas may realize detection of downhole multiple azimuth angles, while exiting of all the antennas may realize downhole omnidirectional detection.

The more the magnet assembly is, the more the antenna is, and therefore there are more detectable sensitive regions. Exciting the antenna at the corresponding location will do when a certain sensitive region needs to be detected. Assume there are four magnets, which are positioned, respectively, east, south, west and north of the center of the probe skeleton in accordance with the compass direction, and the four corresponding antennas are marked as A, B, C and D, respectively. Table 1 illustrates the range of a sensitive region generated by exciting different antennas.

TABLE 1

| Mode | Antenna A | Antenna B | Antenna C | Antenna D | Sensitive regions |
|---|---|---|---|---|---|
| 1 | + | − | − | − | At a single azimuth angle in the east |
| 2 | − | + | − | − | At a single azimuth angle in the south |
| 3 | − | − | + | − | At a single azimuth angle in the west |
| 4 | − | − | − | + | At a single azimuth angle in the north |
| 5 | + | + | − | − | At multiple azimuth angles in the east and the south |
| 6 | + | − | + | − | At multiple azimuth angles in the east and the west |
| 7 | + | − | − | + | At multiple azimuth angles in the east and the north |
| 8 | − | + | + | − | At multiple azimuth angles in the west and the south |
| 9 | − | + | − | + | At multiple azimuth angles in the north and the south |
| 10 | − | − | + | + | At multiple azimuth angles in the west and the north |
| 11 | + | + | + | − | At multiple azimuth angles in the east, the west, and the south |
| 12 | + | + | − | + | At multiple azimuth angles in the east, the south, and the north |
| 13 | + | − | + | + | At multiple azimuth angles in the east, the west, and the north |
| 14 | − | + | + | + | At multiple azimuth angles in the west, the south, and the north |
| 15 | + | + | + | + | Omnidirectional |

In table 1, + indicates an antenna is excited, − indicates an antenna is not excited. It can be seen from table 1 that, exciting different antennas may realize detection of stratum information at different azimuth angles, allowing circumferential resolution of a nuclear magnetic resonance logging instrument probe. When there are 4 antennas, 15 detection modes may be realized, when there are 8 antennas, 255 detection modes may be realized, and more antennas may be added to realize more detection modes.

In downhole detection, detection of stratum information at different axial depths may be realized through lifting the probe up or lowering the probe down; detection of stratum information at different radial depths may be realized through changing excitation frequency of the antenna; and detection of stratum information at different azimuth angles may be realized through exciting different antennas. As a result, signals in the dimension of axial depth, radial depth, and circumferential azimuth angle may be combined to realize detection capability of the probe in the three dimensions. In this embodiment, the axial direction refers to the extension direction of the central axis of a bore, the radial direction refers to the direction in which the bore center extends outwards along a radius, and the circumferential direction refers to the extending direction surrounding the bore center.

In the nuclear magnetic resonance logging instrument probe provided by this embodiment, a plurality of magnet assemblies are evenly distributed in the circumferential direction of the probe skeleton, an antenna is arranged on the outside of each magnet assembly, and each of the plurality of antennas is independently fed, through exciting different antennas, detection of stratum information at different azimuth angles may be realized, thereby improving circumferential resolution of the nuclear magnetic resonance logging instrument probe, and realizing stratum detection in three dimensions in the directions of radius, axis and circumference. Furthermore, each magnet assembly includes at least two layers of magnet which are sequentially arranged from top to bottom, and two adjacent layers of magnet are magnetized in opposite directions, so as to gather magnetic induction lines more close together, and distribute magnetic field strength of a static magnetic field more evenly at the same radial depth and different axial depths, thus improving performance of the nuclear magnetic resonance logging instrument probe.

In this embodiment, layers of the magnet of the magnet assembly may be set according to practical demand, for example, the layers of the magnet of each magnet assembly may be 2 or 4, besides being 3, and no matter what number of the layers of the magnet is, two adjacent layers of magnet are magnetized in opposite directions.

Figure 2:
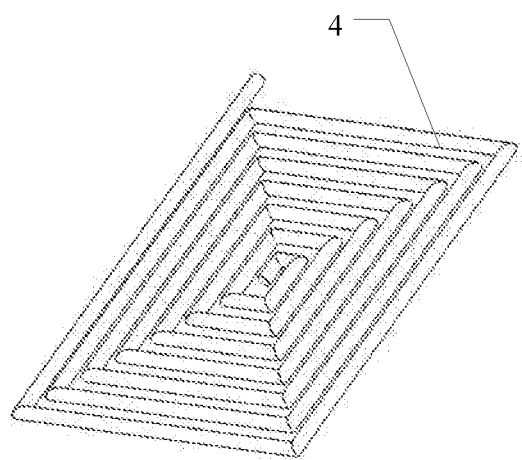
FIG. 2 is a structural diagram for an antenna of nested-multi-hollow-square type of the nuclear magnetic resonance logging instrument probe provided by an embodiment of the present invention.
Figure 3:
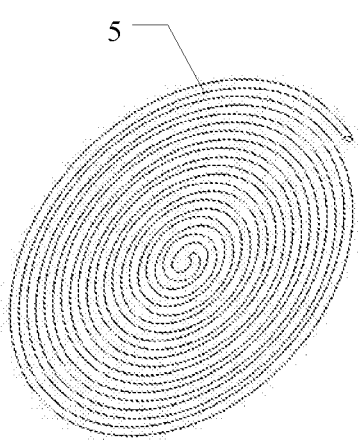
FIG. 3 is a structural diagram for an antenna of nested-multi-hollow-circle type of the nuclear magnetic resonance logging instrument probe provided by an embodiment of the present invention.
Figure 4:
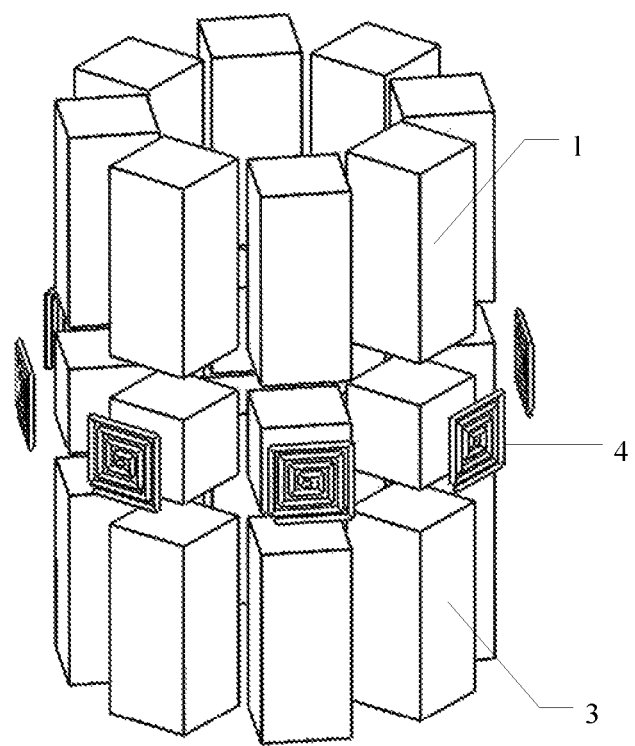
FIG. 4 is a first location diagram for the antenna of nested-multi-hollow-square type and the magnet assembly of the nuclear magnetic resonance logging instrument probe provided by an embodiment of the present invention.
Figure 5:
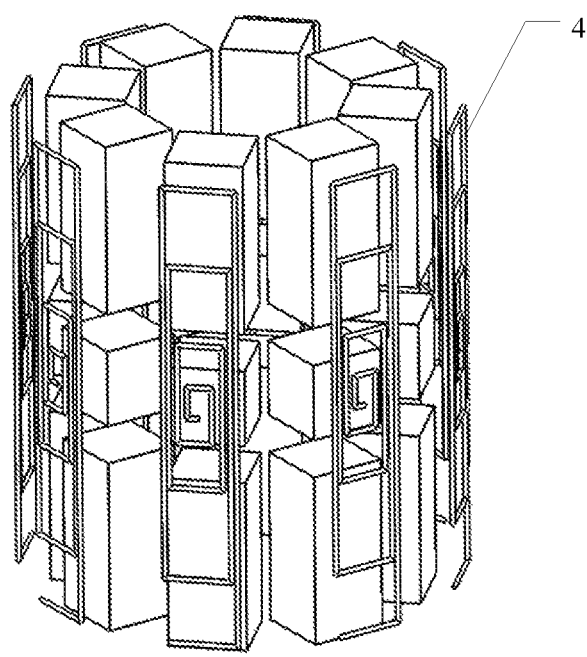
FIG. 5 is a second location diagram for the antenna of nested-multi-hollow-square type and the magnet assembly of the nuclear magnetic resonance logging instrument probe provided by an embodiment of the present invention.

On the basis of the technical solutions provided by the embodiment, preferably, the antenna is formed by winding an oxide-skin-free copper sheet and is of a nested-multi-hollow-square type or a nested-multi-hollow-circle type. FIG. 2 is a structural diagram for an antenna of nested-multi-hollow-square type of the nuclear magnetic resonance logging instrument probe provided by Embodiment 1 of the present invention. FIG. 3 is a structural diagram for an antenna of nested-multi-hollow-circle type of the nuclear magnetic resonance logging instrument probe provided by Embodiment 1 of the present invention. FIG. 4 is a first location diagram for the antenna of nested-multi-hollow-square type and the magnet assembly of the nuclear magnetic resonance logging instrument probe provided by Embodiment 1 of the present invention. FIG. 5 is a second location diagram for the antenna of nested-multi-hollow-square type and the magnet assembly of the nuclear magnetic resonance logging instrument probe provided by Embodiment of the present invention.

As shown in FIG. 4 and FIG. 5, a plurality of nested-multi-hollow-square type antennas 4 may be respectively located outside a plurality of magnet assemblies, and when the antenna is nested-multi-hollow-circle type antenna 5, the nested-multi-hollow-circle type antenna 5 and the magnet assembly may be located likewise. In a radio frequency magnetic field generated by the nested-multi-hollow-square type antenna 4 and the nested-multi-hollow-circle type antenna 5, magnetic induction lines are rather dense, and the magnetic induction lines are perfectly orthogonal to the plane where the antenna is located, facilitating the radio frequency magnetic field being orthogonally matched with the static magnetic field, enabling further improvement in performance of the nuclear magnetic resonance logging instrument probe.

On the basis of the technical solutions provided by the embodiment, preferably, the antenna may include N turns of oxide-skin-free copper sheets, where the distance between a $1^{th}$ and a $2^{th}$ turn equals to that between a $N-1^{th}$ and a $N^{th}$ turn, and the distance between a $k^{th}$ turn and a k+1 th turn is greater than that between the $1^{th}$ and the $2^{th}$ turn; and both k and N are natural numbers, where 1<k<N−1, and N>3.

When feeding the antenna, the magnetic field strength at the center of the radius of the antenna is relatively large. For instance, when there are 10 turns of coils in the antenna, the magnetic field strength on the outside of the $4^{th}$ to $7^{th}$ turn is relatively large, while the magnetic field strength on the outside of the $1^{th}$ turn and the $10^{th}$ are relatively small. And therefore, arranging thin coils at the middle turns of the antenna, and dense ones on the innermost side and the outermost side, allows the antenna to generate more even radio frequency magnetic field.

On the basis of the technical solutions provided by the embodiment, preferably, an auxiliary antenna is arranged on the outside of each of the antennas and is fed independently from the antenna.

In practical operation, separately exciting the antenna or the auxiliary antenna on the outside thereof may detect stratum information in a near region, and exciting the two antennas simultaneously may enable detection of stratum information of a more distant region, thus improving detection capability of the nuclear magnetic resonance logging instrument probe in the radial depth.

On the basis of the technical solutions provided by the aforementioned embodiment, preferably, a plurality of holding cavities may be arranged in the probe skeleton to match with the magnet, and the plurality of the magnet are respectively arranged in the plurality of holding cavities in a fixed manner. Moreover, a plurality of grooves may be processed on the probe skeleton for the plurality of antennas to be respectively arranged therein in a fixed manner. And the groove is filled with material with high magnetic conductivity, which can improve the efficiency of the antenna, and guarantee the depth of the sensitive regions.

On the basis of the technical solutions provided by the aforementioned embodiment, preferably, the solution also includes: an antenna excitation device for feeding the antenna; the antenna excitation device includes a plurality of excitation channels to be electrically connected with the plurality of antennas, respectively. Sensitive region sections at different azimuth angles may be generated by providing an excitation signal to different antennas.

On the basis of the technical solutions provided by the aforementioned embodiment, preferably, a through hole is arranged in the probe skeleton, and the central axis of the through hole coincides with the central axis of the probe skeleton.

For a cable nuclear magnetic resonance logging instrument, a support bracket may be provided which passes through the through hole, and the support bracket is fixedly connected with a probe housing for mechanically supporting the probe; and for a measurements-while-drilling nuclear magnetic resonance logging instrument, a fluid guide pipe may be provided which passes through the through hole for drilling fluid to run through, the fluid guide pipe is fixedly connected with the probe skeleton via a metal piece, and can pump drilling fluid generated during the drilling process out of the borehole.

Embodiment 2

Embodiment 2 of the present invention provides an antenna excitation method based on the nuclear magnetic resonance logging instrument probe described by any one of the above embodiments. In this embodiment, the antenna excitation method may include:

exciting one antenna, in order to realize detection of a downhole single azimuth angle;

exciting at least two antennas, in order to realize detection of downhole multiple azimuth angles; and exciting all the antennas, in order to realize detection of downhole omnidirectional detection.

The principle of the antenna excitation method provided by this embodiment is similar to Embodiment 1 and will not be repeated herein.

In the antenna excitation method provided by the embodiment, through exciting different antennas, detection of stratum information at different azimuth angles may be realized, thereby improving circumferential resolution of the nuclear magnetic resonance logging instrument probe, and realizing stratum detection in three dimensions in the directions of radius, axis and circumference. Furthermore, each magnet assembly includes at least two layers of magnet which are sequentially arranged from top to bottom, and two adjacent layers of magnet are magnetized in opposite directions, so as to gather magnetic induction lines more close together, and to distribute magnetic field strength of a static magnetic field more evenly at the same radial depth and different axial depths, thus improving performance of the nuclear magnetic resonance logging instrument probe.

Finally, it should be noted that, the various embodiments above are intended to describe, rather than limit the technical solutions of the present invention; and although the present invention is detailed referring to the aforementioned embodiments, one of ordinary skill in the art should understand that modifications can be made to the technical solutions recorded by the various embodiments above, or that equivalent substitutions can be made to some or all of the technical features; and these modifications or substitutions shall not make essence of the technical solutions depart from the scope of technical solutions in the embodiments of the present invention.

What is claimed is:

1. A nuclear magnetic resonance logging instrument probe, comprising: a probe skeleton, a plurality of magnet assemblies and a plurality of antennas;

the probe skeleton is of a cylindrical shape, and the plurality of the magnet assemblies are evenly distributed in a circumferential direction of the probe skeleton;

the magnet assembly comprises at least two layers of magnets arranged sequentially from top to bottom, the at least two layers of magnets are magnetized in a radial direction, and two adjacent layers of magnets of the magnet assembly are magnetized in opposite directions; and an antenna is arranged on the outside of each of the magnet assemblies, and each of the plurality of the antennas is independently fed;

the antenna is formed by winding an oxygen free copper sheet, and is of a nested-multi-hollow-square type or a nested-multi-hollow-circle type;

the antenna comprises N turns of oxygen free copper sheets, a distance between a $1^{st}$ and a $2^{nd}$ turn equals to that between a $N-1^{th}$ and a $N^{th}$ turn, and a distance between a $k^{th}$ turn and a $k+1^{th}$ turn is greater than that between the $1^{st}$ and the $2^{nd}$ turn; and wherein, both k and N are natural numbers, and 2<k<N−1, and N>4.

2. The nuclear magnetic resonance logging instrument probe according to claim 1, wherein, an auxiliary antenna is arranged on the outside of each of the antennas and is fed independently from the antenna.

3. The nuclear magnetic resonance logging instrument probe according to claim 1, wherein, each of the magnet assemblies comprises three layers of magnets, the three layers are an upper layer, a middle layer and a lower layer, wherein, thickness of the middle layer magnet is smaller than that of the upper layer magnet and the lower layer magnet.

4. The nuclear magnetic resonance logging instrument probe according to claim 1, wherein, a plurality of holding cavities are arranged in the probe skeleton to match with the at least two layers of magnets, and a plurality of the at least two layers of magnets are respectively arranged in the plurality of holding cavities in a fixed manner.

5. The nuclear magnetic resonance logging instrument probe according to claim 1, wherein, a plurality of grooves are processed on the probe skeleton for a plurality of the antennas to be respectively arranged therein in a fixed manner.

6. The nuclear magnetic resonance logging instrument probe according to claim 1, wherein, further comprising: an antenna excitation device for feeding the antenna;
the antenna excitation device comprises a plurality of excitation channels, and the plurality of antennas are electrically connected with a plurality of the excitation channels, respectively.

7. The nuclear magnetic resonance logging instrument probe according to claim 1, wherein a through hole is arranged in the probe skeleton, and a central axis of the through hole coincides with a central axis of the probe skeleton;
a support bracket is provided which passes through the through hole and is fixedly connected with a probe housing, or, a fluid guide pipe for drilling fluid to run through is provided which passes through the through hole and is fixedly connected with the probe skeleton via a metal piece.

8. An antenna excitation method based on the nuclear magnetic resonance logging instrument probe according to claim 1, comprising:
exciting one antenna, in order to realize detection of downhole single azimuth angle;
exciting at least two antennas, in order to realize detection of downhole multiple azimuth angles; and
exciting all the antennas, in order to realize detection of downhole omnidirectional detection.

9. An antenna excitation method based on the nuclear magnetic resonance logging instrument probe according to claim 2, comprising:
exciting one antenna, in order to realize detection of downhole single azimuth angle;
exciting at least two antennas, in order to realize detection of downhole multiple azimuth angles; and
exciting all the antennas, in order to realize detection of downhole omnidirectional detection.

10. An antenna excitation method based on the nuclear magnetic resonance logging instrument probe according to claim 3, comprising:
exciting one antenna, in order to realize detection of downhole single azimuth angle;
exciting at least two antennas, in order to realize detection of downhole multiple azimuth angles; and
exciting all the antennas, in order to realize detection of downhole omnidirectional detection.

11. An antenna excitation method based on the nuclear magnetic resonance logging instrument probe according to claim 4, comprising:
exciting one antenna, in order to realize detection of downhole single azimuth angle;
exciting at least two antennas, in order to realize detection of downhole multiple azimuth angles; and
exciting all the antennas, in order to realize detection of downhole omnidirectional detection.

12. An antenna excitation method based on the nuclear magnetic resonance logging instrument probe according to claim 5, comprising:
exciting one antenna, in order to realize detection of downhole single azimuth angle;
exciting at least two antennas, in order to realize detection of downhole multiple azimuth angles; and
exciting all the antennas, in order to realize detection of downhole omnidirectional detection.

13. An antenna excitation method based on the nuclear magnetic resonance logging instrument probe according to claim 6, comprising:
exciting one antenna, in order to realize detection of downhole single azimuth angle;
exciting at least two antennas, in order to realize detection of downhole multiple azimuth angles; and
exciting all the antennas, in order to realize detection of downhole omnidirectional detection.

14. An antenna excitation method based on the nuclear magnetic resonance logging instrument probe according to claim 7, comprising:
exciting one antenna, in order to realize detection of downhole single azimuth angle;
exciting at least two antennas, in order to realize detection of downhole multiple azimuth angles; and
exciting all the antennas, in order to realize detection of downhole omnidirectional detection.

\* \* \* \* \*